United States Patent [19]

Burrows et al.

[11] Patent Number: 5,272,056
[45] Date of Patent: Dec. 21, 1993

[54] MODIFICATION OF DNA AND OLIGONUCLEOTIDES USING METAL COMPLEXES OF POLYAZA LIGANDS

[75] Inventors: Cynthia J. Burrows, Stony Brook; Steven E. Rokita, Port Jefferson; Xiaoying Chen, Stony Brook, all of N.Y.

[73] Assignee: The Research Foundation of State University of New York, Albany, N.Y.

[21] Appl. No.: 637,163

[22] Filed: Jan. 3, 1991

[51] Int. Cl.$^5$ ............................................. C12Q 1/68
[52] U.S. Cl. ............................................. 435/6; 514/185; 536/25.33
[58] Field of Search ............................. 435/6; 536/25.33

[56] References Cited

U.S. PATENT DOCUMENTS 4,980,473  12/1990  Barton .................................. 546/10
4,987,227  1/1991  Burrows et al. ................... 540/452

OTHER PUBLICATIONS

R. Hertzberg et al., J. Am. Chem. Soc., vol. 104, pp. 313-315 (1982).
Kasprzak, K., et al., "Enhancement of Hydroxylation and Deglycosylation of 2'-Deoxyguanosine by Carcinogenic Nickel Compounds", Cancer Research 49, 5964-5968 (Nov. 1, 1989).
Kawanishi, S., et al., "Site Specific DNA Damage Induced by Nickel (II) Ion in the Presence of Hydrogen Peroxide", Carcinogenesis 10, 2231-2235 (1989).
Tullius, T. D., Ed., *Metal-DNA Chemistry*, ACS Symposium Series 402, American Chemistry Society, Washington, D.C. (1989).
M. B. Fleisher, et al., "Metal Complexes Which Target DNA Sites: Coupling Recognition to Reactivity," Nucl. Acids Mol. Biol. 2, 65-84 (1988).
Frantz, B., et al., "Inorganic Reagents as Probes for the Mechanism of a Metal-Responsive Genetic Switch," *Metal-DNA Chemistry*, Tullis, T. D., Ed., ACS Symposium Series 402, American Chemical Society, Washington, D.C. 65-84 (1989).

Dervan, P., "Design of Sequence—Specific DNA—Binding Molecules," Science 232, 464-471 (1986).
Sigman, D. S., "Chemical Nucleases," Biochemistry 29, 9097-9105 (1990).
Dreyer, G. T., et al., "Sequence-Specific Cleavage of Single-stranded DNA: Oligodeoxynucleotide-EDTA-Fe(II)," Proc. Nat. Acad. Sci USA 82, 968-972 (1985).
Van Atta, R. B., et al., "On the Chemical Nature of DNA and RNA Modification by a Hemin Model," Biochemistry 29, 4783-4789 (1990).
Barton, J. K., "Metals and DNA: Molecular Left—Handed Complements," Science 233, 727-734 (1986).
Stubbe, J., et al., "Mechanisms of Bleomycin—Induced DNA Degradation," Chem. Rev. 87, 1107-1136 (1987).
Sherman, S. E., et al., "Structural Aspects of Platinum Anticancer Drug Interactions with DNA", Chem. Rev. 87, 1153-1181 (1987).
Maxam, A. M., et al., "A New Method for Sequencing DNA," Proc. Nat. Acad. Sci. USA 74, 560-564 (1977).
Mack, D. P., et al., "Nickel-Mediated Sequence-Specific Oxidative Cleavage of DNA by a Designed Metalloprotein," J. Am. Chem. Soc. 112, 4604-4606 (1990).
Yoon, H., et al., "Catalysis of Alkene Oxidation by Nickel Salem Complexes Using NaOCl Under Phase—Transfer Conditions," J. Am. Chem. Soc. 110, 4087-4089 (1988).

(List continued on next page.)

*Primary Examiner*—Mary E. Ceperley
*Attorney, Agent, or Firm*—Hoffmann & Baron

[57] ABSTRACT

A process is provided for oxidatively modifying nucleic acids containing a target nucleotide. The nucleic acid is contacted with a polyaza metal comlex in the presence of an oxidizing agent so that the nucleic acid is modified at or near the target nucleotide. Also provided are a kit for carrying out the process and a method for treating neoplastic growth by administering to a subject having neoplastic growth, an effective amount of a polyaza metal complex which is capable of modifying DNA.

31 Claims, 2 Drawing Sheets

OTHER PUBLICATIONS

Karn, J. L., et al., "Nickel(II) Complexes of the Tetradentate Macrocycle 2, 12-Dimethyl-3,7,11,17-Tetrazabicyclo (11.3.1) Heptadeca—1 (17), 2,11,13,15—Pentaene," Nature 211, 160, 162 (1966).

Busch, D. H., "Distinctive Coordination Chemistry and Biological Significance of Complexes with Macrocyclic Ligands," Acc. Chem. Res. 11, 392–400 (1978).

Tait, A. M., et al., "2,3-Dimethyl-1,4,8,11-Tetraazacyclo-tetradeca-1,3-Diene (2,3-$Me_2$[14]-1,3-diene-1, 4, 8, 11-$N_4$) Complexes," Inorg. Synth. 18, 27–29 (1978).

Cummings, S. C., et al., "A New Synthetic Route to Macrocyclic Nickel(II) Complexes with Uninegative, Schiff-Base Ligands," Inorg. Chem. 9, 1131–1136 (1970).

Smierciak, R., et al., "A Comparative Study of Steric Effects of Nickel(II) Complexes Containing 12-Membered Macrocyclic Ligands," Inorg. Chem. 16, 2646–2648 (1977).

Jorgensen, K., "Comparative Crystal Field Studies II. Nickel(II) and Copper(II) Complexes with Polydentate Ligands and the Behavior of the Residual Places for Co-Ordination," Acta Chemica Scand. 10, 887–910 (1956).

Wagler, T. R., et al., "Optically Active Difunctionalized Dioxocyclam Macrocycles: Ligands for Nickel-Catalyzed oxidation of Alkenes," J. Org. Chem. 54, 1584–1589 (1989).

Kimura, E. et al., "Novel Nickel(II) Complexes with Doubly Deprotonated Dioxopentaamine Macrocyclic Ligands for uptake and Activation of Molecular Oxygen," J. Am. Chem. Soc. 104, 4255–4257 (1982).

Kimura, E., et al., "Macrocyclic Dioxo Pentaamines: Novel Ligands for 1:1 Ni(II)–$O_2$ Adduct Formation," J. Am. Chem. Soc. 106, 5497–5505 (1984).

Chen, D., et al., "Oxygen Insertion in the Ni(II) Complexes of Dioxopentaaza Macrocyclic Ligands," J. Am. chem. Soc. 112, 9411–9412 (1990).

Kruger, H. J., et al., "Stabilization of Nickel(III) in a Classical $N_2S_2$ Coordination Environment Containing Anionic Sulfur," Inorg. Chem. 26, 3645–3647 (1987).

Dyrssen, D., et al., "On the Complex Formation of Nickel with Dimethylglyoxime," Acta Chemica Scand. 13, 50–59 (1959).

Schultz, P. G., et al., "Design and Synthesis of a Sequence—Specific DNA Cleaving Molecule (Distamycin-EDTA) iron(II)," J. Am. Chem. Soc. 104, 6861–6863 (1982).

Stewart, K. D., "The Effect of Structural Changes in a Polyamine Backbone on its DNA-Binding Properties," Biochem., Biophys. Res. Comm. 152, 1441–1446 (1988).

Yoon, H., et al. "High Turnover Rates in pH-Dependent Alkene Epoxidation Using NaOCl and Square-Planar Nickel(II) Catalysts," J. Am. Chem. Soc. 112, 4568–4570 (1990).

Mack, D. P., et al., "Design and Chemical Synthesis of a Sequence-Specific DNA-Cleaving Protein," J. Am. Chem. Soc. 110, 7472–7574 (1988).

MODIFICATION OF DNA AND OLIGONUCLEOTIDES USING METAL COMPLEXES OF POLYAZA LIGANDS

This invention was made with government support under grant number CHE 9006684 awarded by the National Science Foundation. The government has certain rights in the invention.

The invention relates to the modification of nucleic acids by oxidation using metal complexes of polyaza ligands.

The technique of irreversible DNA modification holds great potential as an in vitro tool for molecular biologists. Such modification raises the possibility of DNA - directed drug therapy in vivo. Currently prescribed chemotherapeutic agents acting at the level of DNA are often effective, but their therapeutic index is poor, limited by the lack of target specificity.

Naturally-occurring and laboratory-designed agents for DNA modification have often relied on transition metal ions for nucleic acid oxidation. For recent reviews see: Metal-DNA Chemistry. Tullius, T. D. Ed., ACS Symposium Series 402, American Chemical Society, Washington, D.C., 1989. Simple metal complexes may themselves show site specificity in their reactions with DNA based on intercalative, groove-binding or hydrogen-bonding interactions of the metal's ligands with the DNA. For example, see Id.,; and M. B. Fleisher, et al., "Metal Complexes Which Target DNA Sites: Coupling Recognition to Reactivity", Nucl. Acids Mol. Biol. 2, 65 (1988). Site-specificity may also result from the intrinsic reactivity of certain bases or sequences with an oxidant. For examples, see Frantz, B. and O'Halloran, T. V., in Metal-DNA Chemistry, Tullius, T. D., Ed., ACS Symposium Series 402, American Chemistry Society, Washington, D.C., 1989, pp 97–105. Alternately, certain metal complexes have been tethered to known DNA-binding drugs or proteins in order to effect site-specificity. For example, see Dervan, P. B., "Design of Sequence-Specific DNA-Binding Molecules". Science 232, 464–471 (1986). The identification of new metal complexes for reactions with DNA through site-specific, non-diffusible species would aid in the development of new sequence-specific or conformation-specific DNA cleaving agents.

Chemical nucleases have been defined as redoxactive coordination complexes that nick nucleic acids under physiological conditions by attack on the ribose or deoxyribose moiety and have been known to include metal complexes such as 1,10-phenanthroline copper complex (Sigman, D. S., "Chemical Nucleases", Biochemistry 29, 9097–9105 (1990)). The chemical nucleases have also been known to include derivatives of ferrous-EDTA (Dreyer, G. B. and Dervan, P. B., "Sequence-Specific Cleavage of Single-Stranded DNA: Oligodeoxynucleotide-EDTA.Fe(II)", Proc. Natl. Acad. Sci. USA 82, 968–972 (1985)), manganese porphyrins (Van Atta, R. B. et al., "On the Chemical Nature of DNA and RNA Modification by a Hemin Model System", Biochemistry 29, 4783–4789 (1990)), and octahedral ruthenium complexes of 4,7-diphenyl-1,10-phenanthroline (Baron, J. K., "Metals and DNA: Molecular Left-Handed Complements", Science 233, 727–734 (1986)).

Antibiotics such as bleomycin and cis-platin are also known to modify DNA. Bleomycin is a structurally complex glycopeptidan which binds to DNA, and in the presence of $Fe^{2+}$ and $O_2$ causes degradation of DNA by single and double-stranded cleavage (Stubbe, J. and Kozarich, J. W., "Mechanisms of Bleomycin-Induced DNA Degradation", Chem. Rev. 87, 1107–1136 (1987)). The bleomycins have been used clinically against certain malignant lymphomas and squamous cell carcinomas. Cis-platin is an antitumor drug which binds to DNA and forms crosslinks (Sherman, S. E., and Lippard, S. J., "Structural Aspects of Platinum Anticancer Drug Interactions with DNA", Chem. Rev. 87, 1153–1181 (1987)). Cisplatin has been used clinically in the treatment of ovarian carcinoma and testicular teratoma.

Other chemicals which have been used to modify DNA and oligonucleotides are dimethyl sulfate, dimethyl pyrocarbonate, osmium tetroxide and permanganate. These chemicals have been known to react preferentially with various nucleotide bases with strand scission upon subsequent treatment with alkaline solution. Many of these reagents, particularly dimethyl sulfate, are known to be quite toxic.

The Maxam-Gilbert Method for sequencing DNA is based on the chemical degradation of single or double-stranded DNA through five separate chemical cleavage reactions, each specific for a type of nucleotide base. (Maxam, A. M. and Gilbert, W., "Sequencing End-Labeled DNA with Base-Specific Chemical Cleavages", Proc. Nat. Acad. Sci. USA 74, 560 (1977)). The DNA to be analyzed is first cleaved with restriction enzymes, the fragments are endlabelled at their termini with [$^{32}$P]phosphate, the fragments are purified, and the purified fragments are modified with chemical treatment. The modifications include methylation of guanine using dimethyl sulfate, depurination of guanine and adenine with formic acid, pyrimidine ring-opening of cytosine and thymine using hydrazine without salt, and ring opening of cytosine using hydrazine with salt (NaCl). Modification is followed by backbone cleavage with piperidine. The cleaved population is then resolved by electrophoresis through polyacrylamide gels, and the end-labeled molecules detected by autoradiography. The present invention is suitable for use in the Maxam-Gilbert protocol.

A complex of a peptide and Ni(II) which requires a DNA-binding protein has been used to mediate DNA cleavage by Mack, D. P. and Dervan, P. B. "Nickel-Mediated Sequence-Specific Oxidative Cleavage of DNA by a Designed Metalloprotein", J. Am. Chem. Soc. 112 4604–4606 (1990). The present invention does not require a DNA-binding protein for site-specific cleavage.

Certain square planar nickel(II) complexes, such as Ni(II)(salen) and Ni(II)(cyclam) have been shown to catalyze oxygen atom transfer chemistry, e.g., olefin epoxidations using iodosylbenzene, NaOCl or $KHSO_5$ as terminal oxidant (Yoon and Burrows, "Catalysis of Alkene Oxidation by Nickel Salen Complexes Using NaOCl under Phase-Transfer Conditions", J. Am. Chem. Soc. 110, 4087–4089 (1988). Such Ni(II) polyamine complexes, however, have not been used in the oxidation of DNA.

Accordingly, it is an object of the invention to provide a DNA, RNA, and nucleic acid modification method using readily available reagents of low toxicity.

It is another object to provide conformation specific cleavage in non-classical duplex structures and unpaired regions such as extra-helical regions, loops, mismatched sites, cruciform structures and unpaired end groups in double-stranded DNA.

It is a further object of the invention to provide a method for cleavage of single-strand DNA at guanine sites.

It is yet another object to provide a new method for guanine-specific cleavage in Maxam-Gilbert sequencing technology.

It is still another object to provide therapeutic methods wherein DNA is modified using polyamine metal complexes.

SUMMARY OF THE INVENTION

Accordingly there is provided a process for oxidatively modifying a nucleic acid comprising the steps of providing a nucleic acid containing a target nucleotide which includes guanine, and providing a polyaza metal complex which is capable of oxidizing the nucleic acid at or near the target sequence in the presence of an oxidizing agent. The nucleic acid is contacted with the polyaza metal complex in the presence of an oxidizing agent so that the nucleic acid is modified at or near the target nucleotide.

Structures for the polyaza metal complex are derivatives of Structures I–III.

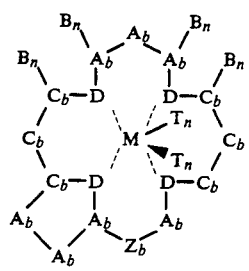

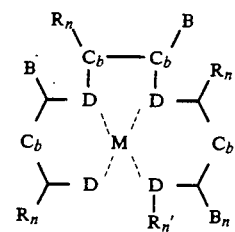

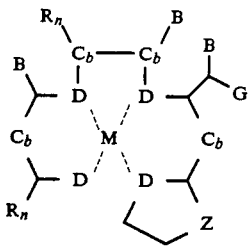

wherein:
A independently represents carbon or oxygen;
B independently represents doubly bonded oxygen;
C represents carbon;
D independently represents nitrogen, oxygen or sulfur;
M represents a metal ion,
T represents an anion which can be replaced by water in solution;
Z independently represents carbon or nitrogen.
b=0–5;
n=0–1;
R independently represents $(CH_2)_3NH_2$, $(CH_2)_4NH_2$,

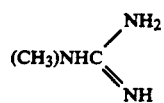

or hydrogen; except that all R radicals in one structure do not represent hydrogen and all n values in $R_n$ in one structure do not equal zero;
R' represents hydrogen, alkyl, aryl or a continued polypeptide chain;
G represents OH, OR, a simple amide or a DNA delivery agent; and wherein all atoms contain sufficient bonds to adjacent atoms, to other atoms or to hydrogen to result in a stable structure.

By independently representing is meant that within one structure, all values for the variables such as A, D, R, b, n, etc. need not be the same, but may represent different atoms or numbers within a single structure. Preferred metals for the complexes are nickel, cobalt and palladium.

The polyaza metal complex of Structures I-III may be structures 1-or derivatives thereof:

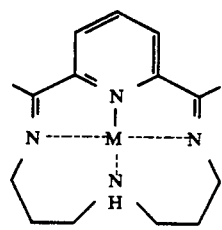

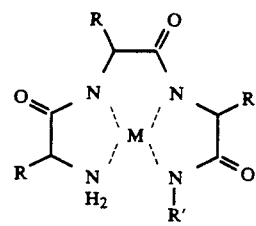

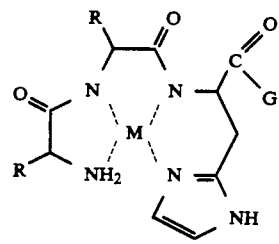

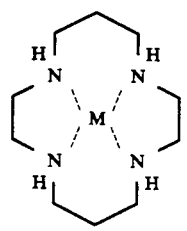

-continued
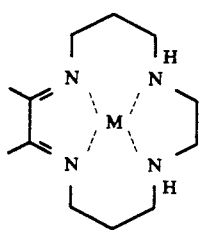
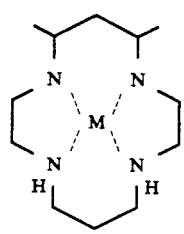
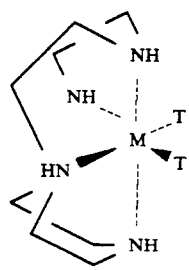
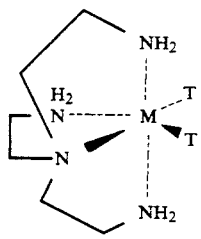
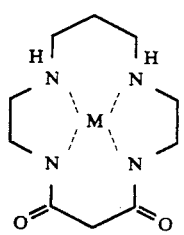
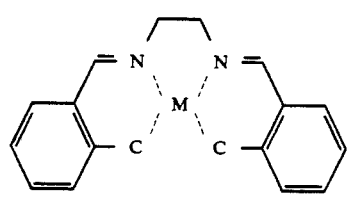
-continued
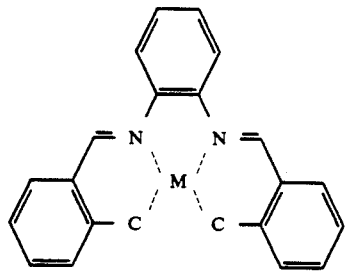
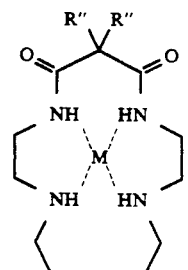
R″ = fluorine, alkyl or aryl
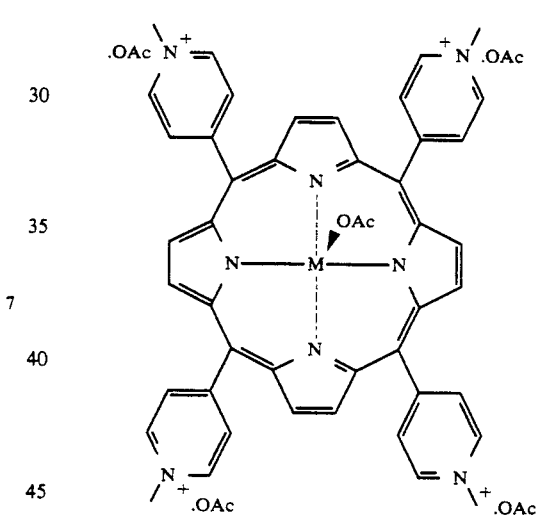
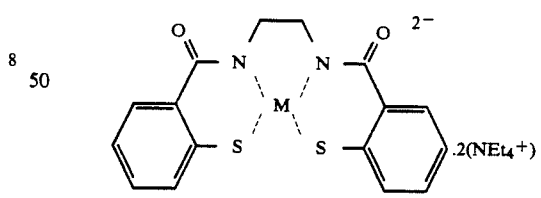
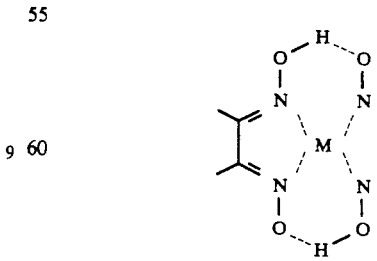
A kit is also provided for a nucleic acid assay for locating guanine groups in nucleic acids, oligonucleotides, polynucleotides, RNA and single-stranded DNA, and non-base paired guanine groups in double-stranded DNA. The kit comprises a polyaza metal complex selected from Structures I-III and their derivatives, an oxidant selected from the group consisting of peracid, hypochlorite, $O_2$, peroxide in combination with ascorbate, $O_2$ in combination with ascorbate, and a base of piperidine, N-butylamine or sodium hydroxide. The detection, for example, of labelled 5'-ends in base-cleaved oligonucleotide indicates the position of guanine groups in the oligonucleotide.

A method is also provided for treating neoplastic growth comprising administering to a subject having a neoplastic growth, an effective amount of a polyaza metal complex of Structures I-III and their derivatives.

Advantageously, the process provides a new method for guanine-specific modification of DNA in sequencing technology and in therapeutics. In addition, the currently used chemical sequencing methods use volatile and toxic chemicals such as dimethylsulfate. The invention employs less toxic materials which are more easily handled.

For a better understanding of the present invention, together with other and further objects, reference is made to the following description, taken together with the accompanying drawings and its scope will be pointed out in the appended claims.

DETAILED DESCRIPTION OF THE INVENTION

Polyaza Compounds

Figure 1:
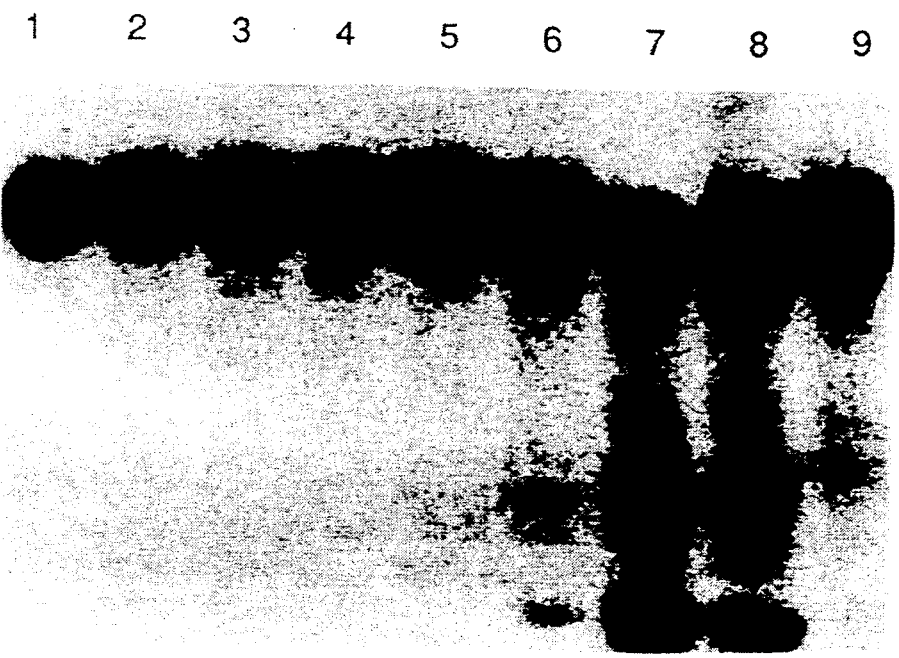
FIG. 1 is an autoradiogram of an electrophoresis of a polyacrylamide gel showing oligonucleotide cleavage products obtained using structure 1 with an oxidant and base treatment compared with control studies.

The compounds useful in the invention are characterized in one regard by their ability to form stable complexes with transition metals. Stable complexes are those having measurable lifetimes at room temperature in water or common organic solvents.

The compounds comprise at least one ligand and a transition metal. A ligand is defined herein as a molecule that is attached to the central metal atom of a coordination compound. Preferred ligands are tetradentate or pentadentate and may comprise either macrocyclic or non-macrocyclic molecules. Other ligands, however, can also be used. It is to be understood that a tetradentate ligand has four donor atoms while a pentadentate ligand has five donor atoms.

The donor atoms may be nitrogen, oxygen, and/or sulfur. Preferably at least two donor atoms are nitrogens, which are separated by from two to four carbon atoms.

Suitable nitrogen donor groups are the amino group of peptides, or amines, imines, pyridines, imidazoles, pyrroles, and pyrazoles, with imine and pyridine groups preferred. The configuration may be square planar or pyramidal, with square planar preferred, but is not limited to these. Suitable oxygen donor groups are phenol, alcohol, carboxylic acid, and carbonyl. Examples of molecules containing oxygen donor groups are salens, salophens and crown thio ethers. Generally, crown ethers containing only oxygen donor groups are not suitable herein. Sulfur donor groups may be, e.g. thiols, thiolates and thiophenols. Complexing molecules containing sulfur groups may contain only sulfur donor groups such as in the crown thio ethers, or the sulfur groups may be combined with oxygen and/or nitrogen donor groups in a suitable ligand.

The ability of the ligands to form stable complexes results from the relative positions of the donor groups. Much of the rest of the ligand consists of carbon atoms that may be thought of as collectively forming a scaffold for maintaining the proper position of the donor groups.

Substituents on the atoms of the ligand affect the properties of the compounds, such as their ability to bind the nucleotides and DNA, their effectiveness in participating in the modification of nucleotides and DNA, their solubility in various solvents, and the stability of the complex they form with transition metals. The atoms of the ligands are normally substituted with sufficient hydrogen atoms to form a stable compound. It should be appreciated, however, that any positions in the ligands, whether or not so indicated herein, may be substituted with any other group and still do substantially the same thing in substantially the same way to accomplish the same result and are, therefore, to be considered equivalent to positions bearing hydrogen atoms as substituents for the purpose of determining the scope of the present invention.

Suitable complexes are derivatives of the ligands shown above as Structures I-III. Illustrative of these are Structures 1-14. Structure 1 is a tetraazabicyclo designated 2,12-dimethyl-2,7,11,17-tetraazobicyclo[11.3.1]heptadeca-1(17),2,11,13,15-pentane metal complex. Synthesis of complexes of this type has been described by Karn, J. L. and Busch, D. H., "Nickel(II) Complexes of the Tetradentate Macrocycle 2,12-Dimethyl-3,7,11,17-Tetraazabicyclo (11.3.1) Heptadeca-1 (17),2,11,13,15-Pentaene", Nature (London) 211, 160-163 (1966).

Structures 2a and 2b are examples of peptide complexes. Any peptide which satisfies the requirement for donor groups can be used. The best peptides for the current work are those including amino acids with positively charged side chains such as lysine, ornithine or arginine so that in Structures 2a and 2b, for R, for example, (CH$_3$)NH$_2$ may be derived from ornithine, (CH$_2$)$_4$NH$_2$ may be derived from lysine, and

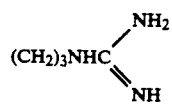

may be derived from arginine. The peptide complexes can be derived from alpha amino acids which are naturally occurring or synthetic. A DNA-cleaving metalloprotein consisting of an alpha amino acid-containing peptide and Ni(II) with the DNA-binding domain of Hin recombinase attached has been described by Mack, D. P. and Dervan, P. B., "Nickel-Mediated Sequence-Specific Oxidative Cleavage of DNA by a Designed Metalloprotein", J. Am. Chem. Soc. 112, 4604, 4606 (1990). In contrast, the peptide metal complexes useful herein have a positive charge and do not require the attachment of Hin recombinase although Hin recombinase can be used.

Other suitable ligands are polyazamacrocycles. A typical polyazamacrocycle capable of complexing transition metal ions is 1,4,8,11-tetraazacyclotetradecane (cyclam). The ability of cyclam and its derivatives to form stable complexes with cobalt, nickel, copper and other metals and to stabilize high oxidation states of these metals has been studied by Busch, "Distinctive Coordination Chemistry and Biological Significance of Complexes with Macrocyclic Ligands", Acc. Chem. Res. 11, 392–400 (1978). A suitable metal complex of this type is shown as structure 3.

Also useful are other polyazamacrocycles such as 2,3-dimethyl-1,4,8,11-tetraazacyclotetradeca-1,3-diene metal complexes shown as structure 4. The synthesis of structure 4 has been described by Tait, A. M. and Busch, D. H., "2,3-Dimethyl-1,4,8-Tetraazacyclotetradeca-1,3-Diene (2,3-Me$_2$[14]-1,3-diene-1,4,8,11-N$_4$) Complexes", Inorg. Synth. 18, 27–29 (1978).

Structure 5 is a (11,13-dimethyl-1,4,7,10-tetraazacyclotrideca-10,12,-dienatonickel(II) compound. Its synthesis in the iodide form is described by Cummings, S. C., and Sievers, R. E., "A New Synthetic Route to Macrocyclic Nickel(ii) Complexes with Uninegative, Schiff-Base Ligands", Inorg. Chem. 9, 1131–1136 (1970). Structure 6 is a Ni(cyclen). Cyclen is commercially available from Parish Chemical Co. The nickel nitrate complex may be prepared according to the procedure of R. Smierciak, et al., "A Comparative Study of Steric Effects of Nickel(II) Complexes Containing 12-Membered Macrocyclic Ligands", Inorg. Chem. 16, 4646 (1977).

Structure 7 is Ni(tren)(X$_2$). The ligand, tren, is commercially available from Aldrich Chemical Co. and the nickel complex may be prepared according to Jorgensen, K., "Comparative Crystal Field Studies II. Nickel-(II) and Copper(II) Complexes with Polydentate Ligands and the Behavior of the Residual Places for Co-Ordination", Acta Chemica Scand. 10, 887–910 (1956). X in structures 6 and 7 is preferably any common anion, such as $Cl_1^-$, $Br_1^-$, $I^-$, $NO_3^-$, $ClO_4^-$, $CH_3CO_2^-$, $PF_6^-$, $BF_9^-$ and is most likely replaced by $H_2O$ when the complex is dissolved in water.

More recently, 1,4,8,11-tetraazacyclotetradecane-5,7-dione (dioxocyclam) has been developed and its ability to form complexes with certain metal ions studied (Wagler, T. R., et al., "Optically Active Difunctionalized Dioxocyclam Macrocycles: Ligands for Nickel-Catalyzed Oxidation of Alkenes", J. Organ. Chem 54, 1584–1589 (1989). These complexes involve the coordination of the metal ions to a deprotonated ligand. The structure of the metal complex of dioxocyclam is shown as structure 8. Complexes of the structure 8 type are described in U.S. patent application Ser. No. 484,102, filed Feb. 23, 1990 now U.S. Pat. No. 4,987,227, issued Jan. 22, 1991 to Burrows, C. J., et al. and entitled "Polyazamacrocycles and Their Metal Complexes and Oxidations Using Same" which is herein incorporated by reference in its entirety.

Other ligands used in the complexes for these reactions include cyclam, N,N'-ethylene-bis(salicylideneamine), also known as salen and 1,2-diaminobenzene-NIN-bis(salicylaldimine), also known as salophen. The structure of Ni(salen) is shown as structure 9 and structure of Ni(salophen) is shown as structure 10. Salen and salophen complexes may be prepared using the method of Poddar, S. N., et al., "Metallic Complexes of Schiff's Base Derived from o-Hydroxyacetophenone and Ethylenediamine", J. Indian Chem. Soc. 40, 489–490 (1963).

Also suitable are dioxopentaaza macrocyclic ligands such as structure 11. Structures of this type have been synthesized by Kimura, E. et al., "Novel Nickel(II) Complexes with Doubly Deprotonated Dioxopentaamine Macrocyclic Ligands for Uptake and Activation of Molecular Oxygen", J. Am. Chem. Soc. 104 4255–4257 (1982) and Kimura, et al., "Macrocyclic Dioxo Pentaamines: Novel Ligands for 1:1 Ni(II)-$O_2$ Adduct Formation", J. Am. Chem. Soc. 106, 5497–5505 (1984). Oxygen insertion into metal complexes of structure 11 have been recently described by Chen. D. and Martell, A. E., "Oxygen Insertion in the Ni(II) Complexes of Dioxopentaaza Macrocyclic Ligands", J. Am. Chem. Soc. 112, 9411–9412 (1990). Preferred groups for R" in structure 11 in the process herein are fluoride, alkyl or aryl groups, especially those containing amine groups as part of the aryl or alkyl chain.

Other suitable ligands are porphyrins such as structure 12. The use of [meso-tetrakis (N-methyl-4-pyridyl)-porphinato]manganese(III) (MnTMPP) with $KHSO_5$ to degrade DNA, RNA and polynucleotides has been described by Van Atta, R. B. et al., "On the Chemical Nature of DNA and RNA Modification by a Hemin Model System", Biochem. 29, 4783–4789 (1990). However, the use of nickel is not suggested.

Other suitable complexes are thiol compounds as shown in structure 13 which may be synthesized according to Kruger, H. J. and Holm, R. H., "Stabilization of Nickel(III) in a Classical $N_2S_2$ Coordination Environment Containing Anionic Sulfur", Inorg. Chem. 26, 3645–3647 (1987), and oxime compounds as shown in structure 14 which may be synthesized according to Dyrssen, D., et al., "On the Complex Formation of Nickel with Dimethylglyoxime", Acta Chem. Scand. 13, 51–59 (1959).

Some of the positions shown in Structures I–III and Structures 1–14 do not appear to be substitutents other than hydrogen. Nevertheless, these positions may be substituted by any organic or inorganic group without significantly affecting the ability of the compound to form a complex with transition metals.

Accordingly, any one or more of these positions may be substituted by an inorganic substituent, such as a doubly bonded oxygen, i.e., carbonyl, or a singly bonded oxygen i.e., hydroxy. Some additional inorganic groups include, for example, amino, thio, halo, i.e., F, Cl, Br, and I, etc.

Organic substituents include, for example, alkyl, aryl, alkylaryl and arylalkyl. The alkyl groups may be branched or unbranched and contain 20 carbon atoms or less, preferably 8 carbon atoms or less, and more preferably 4 carbon atoms or less. Some typical examples of alkyl groups include methyl, ethyl, n-propyl, isopropyl, n-butyl, sec-butyl, tert-butyl, isobutyl, and octyl. The alkyl groups may, in whole or in part, be in the form of rings such as cyclopentyl, cyclohexyl, cycloheptyl and cyclohexylmethyl. The cyclic groups described above may be further substituted with inorganic, alkyl, or aryl groups. Any of the alkyl groups described above may have one or more double or triple bond. Moreover, any of the carbon atoms of the alkyl groups may be separated from each other or from the ring nucleus with groups such as carbonyl, oxycarbonyl, oxy, amino, thio, etc. Alkyl groups may also terminate with groups such as halo, hydroxy, amino, carboxy, etc.

Aryl substituents are typically phenyl, but may also be any other aryl groups such as, for example, pyrrolyl, furanyl, thiophenyl, pyridyl, thiazolyl, etc. The aryl group may, further, be substituted by an inorganic, alkyl, or other aryl group. The alkylaryl and arylalkyl groups may be any combination of alkyl and aryl groups. These groups may be further substituted.

Particularly important substituent groups which may be present on the ligands are appended groups which are capable of binding to DNA or nucleotides. These will be called delivery agents. Suitable delivery agents may be of different types including intercalators, groove-binding agents, oligonucleotides, proteins or protein fragments, and polyamines. The intercalators include ethidium, methidium, acridine, proflavin, phenanthroline, etc. The groove-binding agents include distamycin and netropsin. A distamycin derivative was used to direct nucleotide scission by Schultz, P. G., et al., "Design and Synthesis of a Sequence-Specific DNA Cleaving Molecule. (Distamycin-EDTA)iron(II)", J. Am. Chem. Soc. 104, 6861-6863 (1982). Oligonucleotides may bind producing double helical or triple helical areas. Proteins or protein fragments which bind DNA include Hin recombinase (Mack, D. P. and Dervan, P. B., "Nickel-Mediated Sequence-Specific Oxidative Cleavage of DNA by a Designed Metalloprotein", J. Am. Chem. Soc. 112, 4604-4606 (1990)). The useful polyamines include spermine and spermidine described by K. D. Stewart, "The Effect of Structural Changes in a Polyamine Backbone on its DNA-Binding Properties", Biochem, Biophys. Res. Comm. 152, 1441-1446 (1988).

The Complexes

Ligands to be used in the invention form stable complexes with transition metal ions. For the purpose of this specification, transition metals are to be understood as including metals having partly filled d or f shells in any of their commonly occurring oxidation states. The useful transition metals include ions of Ni, Co, Cu, Rh, Pd, Ir, Pt, Cr, Mn, Fe, Ru, and Os. Preferred are ions of Ni, Co and Pd. Most preferred is Ni.

The complexes are formed by contacting a salt of the metal ion with the ligand in a suitable solvent, for example, water and methanol. Progress of the complexation is easily followed visually or spectrophotometrically. Depending upon reaction conditions such as the ligand, the metal, the pH, and the solvent, the complexation reaction may occur rapidly at room temperature, or may require heating.

The complexes may be four, five or six coordinate with four preferred and square planar most preferred.

The complexes may be deprotonated, but an overall positive charge is preferred, and a highly positive charge is most preferred. Balancing anions, counterions, or salts may be as known to those skilled in the art, such as derivatives of salts e.g. perchlorate, acetate, nitrate, chlorides, bromides, iodides, and tetrachlorozincate ($ZnCl_4^{-2}$).

The ligand-metal complexes are used in the process of the invention to modify oligonuoleotides, single-stranded DNA, non-classical duplex structures and double-stranded DNA having particular conformations, that is, extra-helical areas, cruciform DNA, abasic (non base paired G's) areas, unpaired ends, and telomeres (ends of chromosomes). In double stranded DNA, the modification is specific to these conformational areas. The oligonucleotides may be naturally occurring or synthetic. The single-stranded DNA may also be derived from separation of duplex DNA. All forms of RNA are targets for reaction also.

A non-diffusible species is important for site-specificity in the target nucleotide. In contrast, certain complexes, e.g. Fe(II)-EDTA, generate hydroxyl radicals which react with DNA non-specifically. In this type of non-preferred complex, the complex attaches to a binding site and generates a reactive species which diffuses with a loss of specificity. In the system described herein, the metal complex binds to a particular DNA site and the reactive agent is produced at that site when oxidant is present. A non-diffusible species is one which reacts with DNA before it is released from the specific binding site.

The complexes are used to modify or nick DNA or nucleotides when used with an oxidant. Some examples of oxidizing agents include peracids such as peroxymonosulfate salts, e.g. potassium peroxymonosulfate ($KHSO_5$) which is commercially available under the trademark OXONE, magnesium monoperoxyphthalate (MMPP), peroxide, alkylhydroperoxide, $O_2$, hypochlorite, and peroxide or oxygen in combination with ascorbate. Particularly preferred are peroxymonosulfate, MMPP and $O_2$. In physiological systems, oxygen is preferred.

After oxidation, excess oxidant may be quenched with a reductant such as sodium sulfite, and base treatment may be used for cleavage. Suitable bases are piperidine, N-butylamine and sodium hydroxide with a pH of about 9-13.

Reaction conditions include a temperature from about zero to about 100° C., from about 20° C. to about 40° C. preferred and 25°-37° C. most preferred. Reaction time is at least about 30 seconds, from about 10 minutes to an hour preferred and from about 15 minutes to about 30 minutes most preferred. The reaction may be left for an extended period of time, e.g. up to 48 hours without adverse effects. The pH may be about 3-10, with 6.5-7.5 preferred.

For a reaction involving, for example, a nucleotide concentration of about 0.1 to about 50 picomoles of labelled 5'-ends, the metal complex may be used in an amount of from about 0.1 µM to about 10 mM, with from about 0.5 µM to about 100 µM preferred and from about 1µM to about 10 µM most preferred. The oxidant may be used in an amount of from about 0.1 µM to about 10 mM with about 50 µM to about 100 µM preferred. The ratio of metal complex to oxidant may range from about 99:1 to about 1:99. The oxidant is preferably in excess of the metal complex with a ratio of metal complex:oxidant ranging up to about 1:10,000, with from about 1:1 to about 1:50 preferred and 1:1 to 1:2 most preferred.

In vitro, the nucleotide or DNA is labelled in any suitable manner such as with radiolabel, and standard electrophoresis and autoradiography may be used to determine the level of modification.

The process of the invention for modifying DNA or sequencing is suitable for being attained using a kit. The kit may comprise a polyaza metal complex to be used with an oxidant and a base. The kit can supply a polyaza metal complex in an amount of from about 1 to about 3000 nanomolar metal complex, preferably from about 10 to about 300 nanomolar metal complex and most preferably about 25 to about 75 nanomolar of the metal complex. An oxidant is selected from the group consisting of peracid, hypochlorite, $O_2$, peroxide in combination with ascorbate and $O_2$ in combination with ascorbate. The preferred oxidants are oxone, magnesium monoperoxyphthalate, peroxide and alkylhydroperoxide. The most preferred oxidant is oxone. If the kit is to be used in an in vivo system, e.g., in tissue culture or in an animal, the oxidant is preferably provided by dissolved oxygen already present in the system. A base may also be provided, and may be piperidine, N-butylamine or sodium hydroxide having a pH of about 9–13.

The process of the invention can also be used therapeutically to treat neoplasia in the same manner as bleomycin and cis-platin. Neoplasia may occur, for example, in animals such as mammals including humans. Neoplasia is progressive, uncontrolled cell division which, if the progeny cells remain localized at least initially, results in the formation of an abnormal growth which may be called a tumor or neoplasm. A neoplasm may be malignant or benign. A malignant neoplasm invades adjacent tissues and may metastasize. A neoplastic growth is generally considered to be a non-inflammatory mass formed by the growth of new cells and having no physiological function. The polyaza metal complexes of the invention can be formulated per se in pharmaceutical preparation or formulated in the form of pharmaceutically acceptable salts. These preparations can be prepared according to conventional chemical methods. Antibiotics such as bleomycin have used therapeutically in humans and have been administered intravenously, intramuscularly or subcutaneously. They are believed to interfere with a rapid cell division which occurs in neoplasia. When the invention is used in a physiological system, e.g. in vivo, it is contemplated that the physiological system provides the $O_2$ necessary to act as the oxidant so that the polyaza metal complex modifies DNA and interferes with replication, thereby affecting cell growth. The DNA modification necessary to interfere with replication may comprise oxidative damage in the DNA caused by the process of the invention. The metal complexes of the invention have the advantage of being less toxic.

EXAMPLES

As the experimental approach, a series of square planar nickel(II) and copper(II) complexes were investigated for their ability to react with DNA. Some of these complexes had been shown previously to catalyze olefin epoxidation using iodosylbenzene, NaOCl or oxone as the terminal oxidant (Yoon, H. et al., "High Turnover Rates in pH-Dependent Alkene Epoxidation Using NaOCl and Square-Planar Nickel(II) Catalysts", J. Am. Chem. Soc. 112, 4568–4570 (1990). In the case of olefin epoxidation, the ability of $Ni^{II}$ complexes to catalyze oxygen atom transfer chemistry was found to be highly ligand dependent.

Oligonucleotides were chosen for study since they are small enough to permit a detailed study yet large enough to display the base specificity for nucleotide oxidation.

Reactions were carried out using a purified oligonucleotide with the 15-base sequence d(CATGCG-CTACCCGTG). The 5'-terminus was labelled with $^{32}P$-phosphate for analysis by gel electrophoresis and autoradiography. Samples of the oligonucleotide were incubated with various metal complexes and an excess of oxidant, either oxone, MMPP, or a 1:1 mixture of $H_2O_2$/ascorbate.

EXAMPLE 1

The pyridine-containing Schiff base complex 2,3-dimethyl-1,4,8,11-tetraazacyclotetradeca-1,3-diene nickel(II)$^{2+}$, i.e., (NiL$_1{}^{2+}$) (structure 1) was prepared according to the method described by Karn, J. L. and Busch, D. H., Nature (London) 211, 160–163 (1966). The complex was tested for its ability to cleave the oligonucleotide described above.

Samples of aqueous solutions containing 3 μM oligonucleotide (10nCi)DNA, 3 μM metal complex and 100 μM MMPP were prepared in a volume of 100 μL, buffered to pH 7.0 (10 mM potassium phosphate, 100 mM NaCl), maintained under ambient conditions and quenched after 30 minutes with 20 mM $Na_2SO_3$.

The samples were individually dialyzed against 1 mM EDTA at pH 8 (2×3h.) and water (1×12h.), lyophilized, treated with 0.2M piperidine for 30 min. at 90° C., lyophilized again, and resuspended in 80% formamide for electrophoresis.

Similar solutions were prepared with NiL$_1{}^{2+}$(no oxidant); oxidants 1:1 $H_2O_2$/ascorbate, MMPP and oxone; NiL$_1{}^{2+}$with 1:1 $H_2O_2$/ascorbate; and NiL$_1{}^{2+}$with oxone. The solutions were prepared in the same manner as the NiL$_1{}^{2+}$and MMPP solutions described above.

Autoradiograms of 20% polyacrylamide gels (denaturing 7M urea) were prepared showing the cleavage products obtained using NiL$_1{}^{2+}$, MMPP and piperidine. The results are shown in FIG. 1.

Lane 1 shows NiL$_1{}^{2+}$only with no oxidant. Lanes 2–4 show the control studies with oxidants alone: $H_2O_2$/ascorbate, MMPP and oxone, respectively. Lane 5 shows NiL$_1{}^{2+}$with 1:1 $H_2O_2$/ascorbate. Lane 6 shows NiL$_1{}^{2+}$with MMPP. Lane 7 shows NiL$_1{}^{2+}$with oxone. Lane 8 is the reference G-lane. Lane 9 shows NiL$_1{}^{2+}$with oxone with omission of piperidine treatment.

Lane 7, representing the reaction of structure 1 with 3 μM NiL$_1{}^{2+}$and 100 μM oxone, exhibits a fragmentation pattern equivalent to that of the Maxam-Gilbert G-lane (lane 8). Cleavage products were observed only after treatment with piperidine (compare lanes 7 and 9). Control studies verified that neither the nickel complex alone nor the oxidants alone generated base-labile products (lanes 1–4) and a comparison of oxidants (lanes 5–7) showed that oxone produced the most reaction with DNA. This example leads to the conclusion that certain Ni-ligand complexes are excellent promoters of oxidative DNA modification at G residues giving rise to base-specific cleavage upon alkaline work-up.

EXAMPLE 2

Various metal complexes were tested for their efficacy for cleavage of the oligonucleotide using KHSO$_5$ as oxidant. Reaction conditions were as described in Example 1 and included 3 μM of metal complex, 3 μM of nucleotide, 100 μM of KHSO$_5$ and piperidine treatment. Autoradiograms of 20% polyacrylamide gels (denaturing 7M urea) were prepared.

The metal complexes were 1) Ni(OAc)$_2$, 2) NiL$_1{}^{2+}$, 3) CuL$_1{}^{2+}$, 4) Ni-GGH (NiL$_2$), 5) Cu-GGH (CuL$_2$), 6) [Ni(cyclam)]$^{2+}$(NiL$_1{}^{2+}$), 7) [Cu(cyclam)]$^{2+}$(CuL$_3{}^{2+}$), 8) NiL$_4{}^{2+}$, 9) NiL$_5{}^+$, 10) Ni(cyclen) (NO$_3$)$_2$(NiL$_6$X$_2$), 11) Ni(tren) (OAc)$_2$(NiL$_7$X$_2$), and 12) Cisplatin (cis-Pt(NH$_3$)$_2$Cl$_2$). The complexes were as follows:

Ni(CH$_3$COO)$_2$      1.

Figure 2:
FIG. 2 is an autoradiogram of an electrophoresis of a polyacrylamide gel comparing efficacy of various metal complexes in the cleavage of the oligonucleotide.

-continued
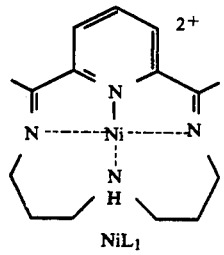
NiL₁
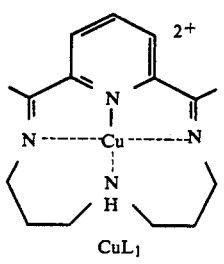
CuL₁
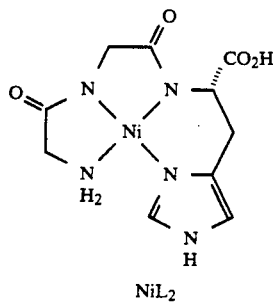
NiL₂
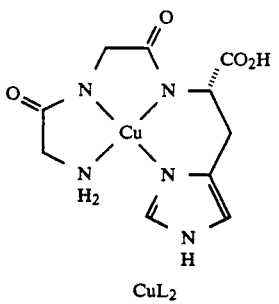
CuL₂
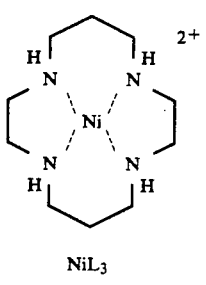
NiL₃
-continued
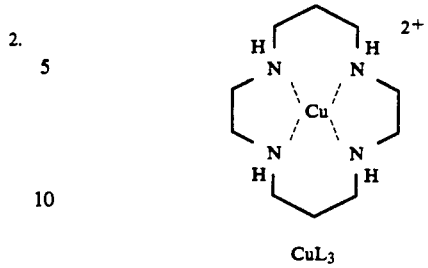
CuL₃
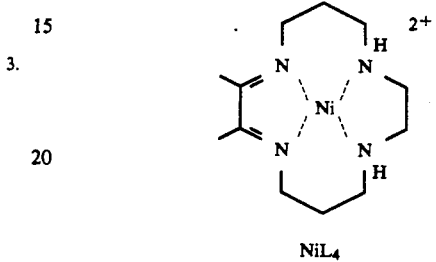
NiL₄
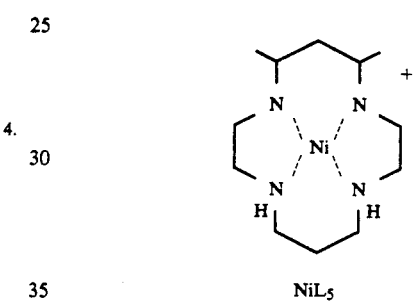
NiL₅
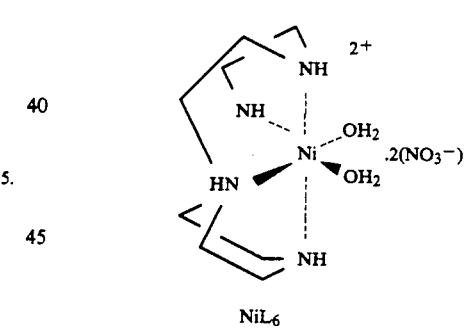
NiL₆
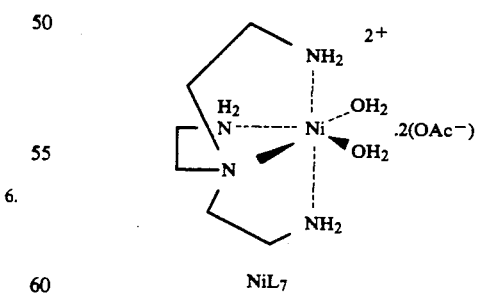
NiL₇
Cisplatin
The results are shown in FIG. 2. Lane 1 shows Ni-(OAc)₂. Lane 2 shows NiL₁²⁺. Lane 3 shows CuL₁²⁺. Lane 4 shows NiL₂. Lane 5 shows CuL₂. Lane 6 shows NiL₃²⁺. Lane 7 shows CuL₃²⁺. Lane 8 shows NiL₄²⁺. Lane 9 shows NiL₅⁺. Lane 10 shows Ni(cyclen)-

(NO$_3$)$_2$. Lane 11 shows Ni(tren)(OAc)$_2$. Lane 12 shows cisplatin.

A qualitative comparison of Ni$^{II}$ complexes showed that the pyridine-containing Schiff base complex NiL$_1^{2+}$ was the most active followed by NiL$_4^{2+}$, another Schiff base complex (compare lanes 2 and 8) and NiL$_3^{2+}$ was less active than these (lane 6). The Ni$^{II}$ and Cu$^{II}$ complexes of the tripeptide GGH, NiL$_2$ and CuL$_2$ have been demonstrated by Mack, D. P., et al., "Design and Chemical Synthesis of a Sequence-Specific DNA-Cleaving Protein", J. Am. Chem. Soc. 110, 7572 (1988) and Mack D. P. and Dervan, P. B., "Nickel-Mediated Sequence-Specific Oxidative Cleavage of DNA by a Designed Metalloprotein", J. Am. Chem. Soc. 112, 4604–4606 (1990) to give highly site-specific DNA cleavage when the tripeptide is appended to a DNA-binding protein fragment. In the present example, however, neither NiL$_2^-$ or CuL$_2^-$ led to significant amounts (lanes 4 and 5). Apparently these anionic square planar metal complexes do not interact sufficiently with DNA and the oxidant in the absence of a DNA-binding agent to yield substantial DNA reactivity. Accordingly, the three reactive Ni$^{II}$ complexes are those which carry a 2+ charge and are square planar complexes of neutral tetradentate ligands. For comparison, the monocationic complex NiL$_{5+}$ was tested and slight evidence of reaction was observed in comparison to background (lane 9). The octahedral complexes [NiL$_6$(H$_2$O$_2$)]$^{2+}$ and [NiL$_7$(H$_2$O$_2$)]$^{2+}$ (lanes 10 and 11) were detectably active under the same conditions. Finally, comparison was made with the DNA-binding drug cis-platin which has been shown to bind to N-7 of guanines. No evidence of G-specific oxidative reactivity was obtained (lane 12).

The results of the examples showed that square planar Ni$^{II}$ complexes of tetraazamacrocycles such as the Schiff base complex NiL$_1^{2+}$ and nickel cyclam NiL$_3^{2+}$ were highly active agents for DNA modification under oxidative conditions compared to related copper complexes or octahedral Ni$^{II}$ complexes. Both KHSO$_5$ (oxone) and magnesium monoperoxyphthalate (MMPP) were effective as oxidants, and peracetic acid had a lesser activity while H$_2$O$_2$ with ascorbate was not effective under these conditions. Furthermore, oxidative DNA modification leading to strand scission after alkaline treatment occurred with high base-specificity for guanine.

The most successful ligands, L$_1$, L$_3$ and L$_4$ are those which provide an intermediate ligand field strength stabilizing square planar or octahedral coordination geometries and rendering Ni$^{II}$ highly Lewis acidic. The stronger ligand field of GGH might inhibit coordination of additional ligands in the axial positions, and the overall anionic complex, NiL$_2^-$ would have less electrostatic attraction to the polyanionic oligonucleotide.

EXAMPLE 3

The procedure of Example 2 is repeated except that the oxidants of Example 2 are omitted and O$_2$ is naturally present in the sample solutions at a concentration of about 300 µM.

The results are expected to be comparable to the results of Example 2. This is intended to show that oxygen can act as the terminal oxidant in the process of the invention.

The use of O$_2$ as a source of dioxygen in Ni(II) complexes was shown by Chen, D. and Martell, A. E., "Oxygen Insertion in the Ni(II) Complexes of Dioxopentaaza Macrocyclic Ligands", J. Am. Chem. Soc. 112, 9411, 9412 (1990), but modification of DNA was not suggested therein.

EXAMPLE 4

The procedure of Example 2 was repeated except that double-stranded DNA was used, at the same concentration of 5'-labelled ends as before. Reaction with metal complex and oxidant and final alkaline treatment and analysis were the same. The results indicate that G sites at the end of an oligonucleotide or in non-base paired regions are more reactive than normal base paired G sites.

EXAMPLE 5

The procedure for Example 4 was repeated except that the double-stranded DNA was heat denatured prior to reaction and analysis. This was done by heating the sample to 90° C. for 5 min, rapid cooling to 4° C. in an ice bath, and immediate reaction with metal complex and oxidant as described above. Analysis showed strand scission at all G-sites analogous to that obtained for single-stranded oligonucleotides. This method would be of use in DNA sequencing techniques for the location of G's.

EXAMPLE 6

In vivo Studies

A procedure analogous to that described in Antholine, et al., "Studies on the Chemical Reactivity of Copper Bleomycin", J. Inorg. Biochem. 17, 75, (1982) for copper bleomycin is used. Erlich cells removed from mice are centrifuged, washed, and resuspended in MEM (minimal essential medium, available from GIBCO). The metal complex such as 11 is added at time zero at a concentration of 0.1–100 nmol complex per mg cell protein (10 nmol preferred). The reaction mixture is incubated at 37° C. in a Gyrotory water bath shaker. Uptake is halted by immersion of aliquots of suspension in ice-water slush, and the supernatant is separated from cells by centrifugation. Cells are washed once in 0.15M NaCl and separated again for analysis. Analysis can be carried out in two ways.

(1) Cells are monitored for a period of up to 72 hours to look for cell proliferation. Diminished cell proliferation compared with controls indicates effectiveness of the metal complex as a drug.

(2) Inhibition of DNA synthesis can be monitored by incubating with tritiated thymine, followed by washing, isolation of the DNA and analysis for amount of incorporated radiolabel. Diminished incorporation compared with control studies indicates effectivenss of the metal complex for DNA damage.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A process for oxidatively modifying nucleic acids selectively at guanine comprising:
   (a) providing a nucleic acid which comprises guanine;
   (b) providing a metal complex having tetradentate or pentadentate organic ligands which is capable of oxidizing the nucleic acid selectively at guanine in the presence of an oxidizing agent, said metal complex being selected from the group consisting of Structures I-III:

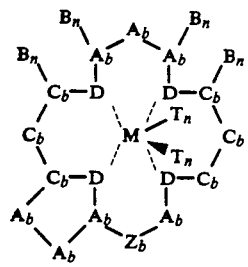

I

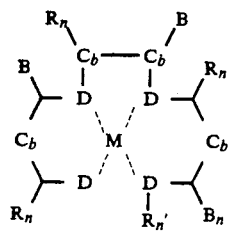

II

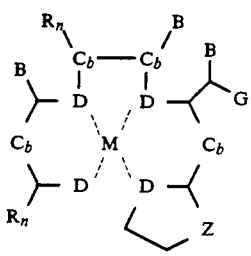

III wherein:
A independently represents carbon or oxygen;
B independently represents doubly bonded oxygen;
C represents carbon;
D independently represents nitrogen, oxygen or sulfur;
M represents a metal ion;
T represents an anion which can be replaced by water in solution;
Z independently represents carbon or nitrogen;
B=0-5;
n=0-1;
R independently represents (CH$_2$)$_3$NH$_2$, (CH$_2$)$_4$NH$_2$,

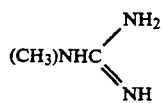

or hydrogen; except that all R radicals in one structure do not represent hydrogen and all n values in R$_n$ in one structure do not equal zero;
R' represent hydrogen, alkyl, or aryl;
G represents OH, OR, a simple amide or a DNA delivery agent;
wherein all atoms A, B, C, D, M, T, Z, R, R' and G depicted in Structures I-III contain sufficient bonds to adjacent A, B, C, D, M, T, Z, R, R' or G atoms, to hydrogen or to other atoms which are substituents which can substitute for hydrogen and are selected from the group consisting of carbonyl, hydroxy, amino, thio, halo, alkyl of 20 carbon atoms or less and phenyl, to result in a stable structure; and (c) contacting the nucleic acid with the metal complex in the presence of the oxidizing agent so that the nucleic acid is oxidized at guanine.

2. The process of claim 1 wherein the metal complex is selected from the group consisting of Structures 1-11, 13, 14:

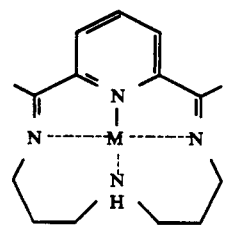

1

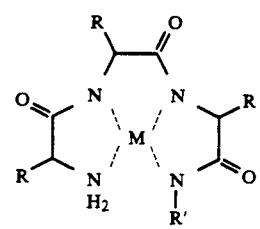

2a

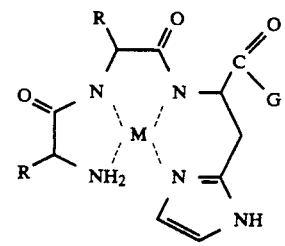

2b

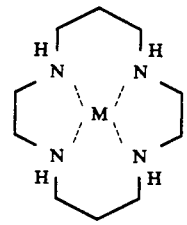

3

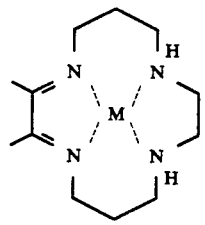

4

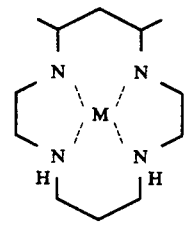

5

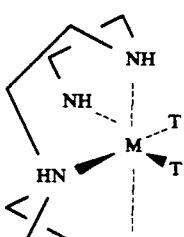

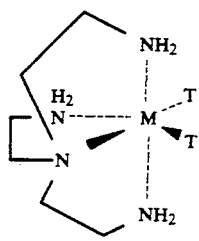

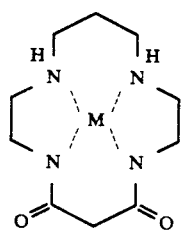

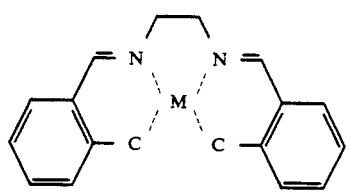

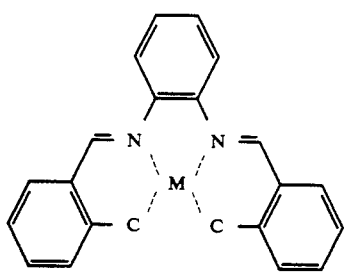

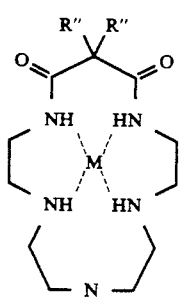

R″ = fluorine, alkyl or aryl

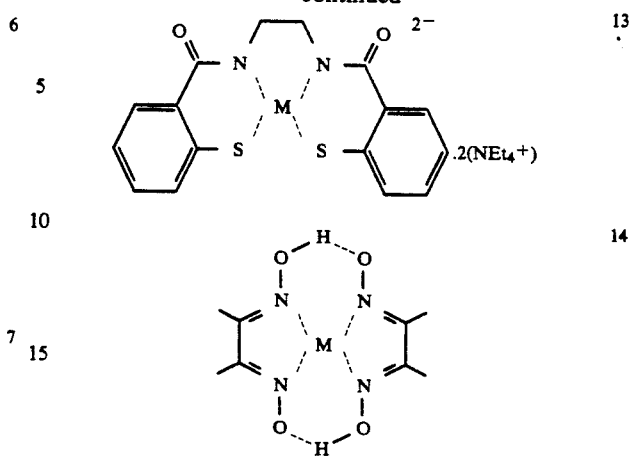

3. The process of claim 1 wherein the metal is selected from the group consisting of $Ni^{2+}$, $Co^{2+}$, $Cu^{2+}$, $Rh^{+2}$, $Pd^{2+}$, $Ir^{2+}$, $Pt^{2+}$, $Cr^{2+}$, $Mn^{2+}$, $Fe^{2+}$, $Ru^{2+}$ and $Os^{2+}$.

4. The process of claim 1 wherein the metal is selected from the group consisting of $Ni^{2+}$, $Co^{2+}$ and $Pd^{2+}$.

5. The process of claim 1 wherein the structure of the metal complex includes a delivery agent selected from the group consisting of intercalators, groove-binding agents, oligonucleotides, protein fragments, and polyamines.

6. The process of claim 5 wherein the intercalator is selected from a group consisting of ethidium, methidium, acridine, proflavin and phenanthroline.

7. The process of claim 5 wherein the groove-binding agent is distamycin or netropsin.

8. The process of claim 5 wherein the oligonucleotide has a nucleotide sequence which enables it to form a double or triple helical areas with the target nucleotide.

9. The process of claim 5 wherein the protein fragment is derived from Hin recombinase.

10. The process of claim 5 wherein the ligand is connected to a polyamine spermine or spermidine.

11. The process of claim 1 wherein the oxidizing agent is selected from the group consisting of peracid, hypochlorite, $O_2$, peroxide in combination with ascorbate, and $O_2$ in combination with ascorbate.

12. The process of claim 11 wherein the peracid is selected from the group consisting of potassium peroxymonosulfate, magnesium monoperoxyphthalate, peroxide and alkylhydroperoxide.

13. The process of claim 1 which further comprises treating the contacted nucleic acid with a base solution so that the nucleic acid is cleaved.

14. The process of claim 13 wherein the base solution is selected from the group consisting of piperidine, N-butylamine and sodium hydroxide.

15. The process of claim 1 which further comprises adding a reductant to the product of step (c).

16. The process of claim 15 wherein the reductant is sodium sulfite.

17. The process of claim 1 wherein the process is carried out in vitro and the nucleotide is labelled with radiolabel.

18. The process of claim 1 wherein the nucleic acid is selected from the group consisting of natural and synthetic nucleotide, oligonucleotide, polynucleotide, RNA, single-stranded DNA, DNA derived from separation of duplex DNA, and double-stranded DNA containing unpaired and non-classically paired guanine base.

19. A process for oxidatively modifying nucleic acids comprising:
   (a) providing nucleic acid which comprises guanine;
   (b) providing a polyaza metal complex which is capable of oxidizing the nucleic acid at or near the target nucleotide in the presence of an oxidizing agent, said polyaza metal complex selected from the group consisting of Structures 1, 3 and 4 and derivatives thereof in which hydrogen is substituted for by a member of the group consisting of carbonyl, hydroxy, amino, thio, halo, alkyl of 20 carbon atoms or less and phenyl

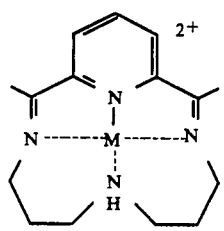

1

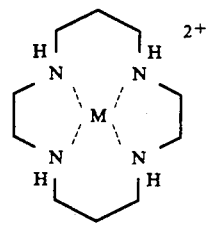

3

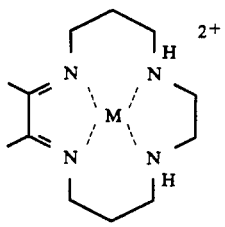

4 wherein $M = Ni^{2+}$, $Co^{2+}$ or $Pd^{2+}$; and
   (c) contacting the nucleic acid with the polyaza metal complex in the presence of an oxidizing agent selected from the group consisting of peracid, hypochlorite, $O_2$, peroxide in combination with ascorbate and $O_2$ in combination with ascorbate, so that the nucleic acid is oxidized selectively at guanine.

20. The kit of claim 21 wherein the metal complex is selected from the group consisting of Structures 1-14.

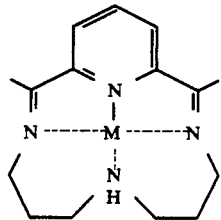

1

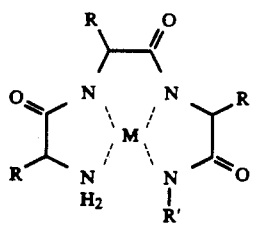

2a

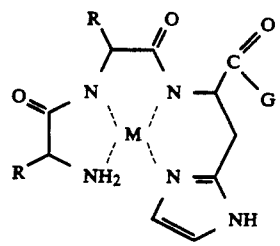

2b

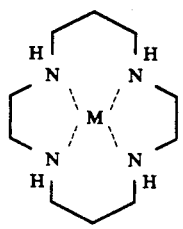

3

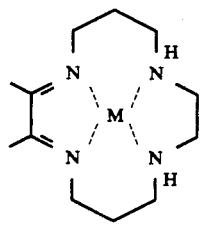

4

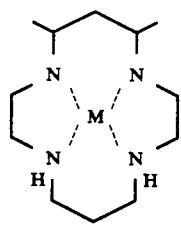

5

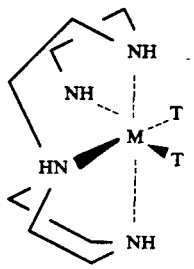

6

-continued

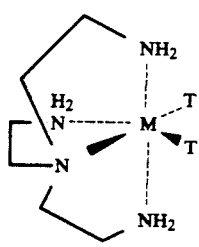

7

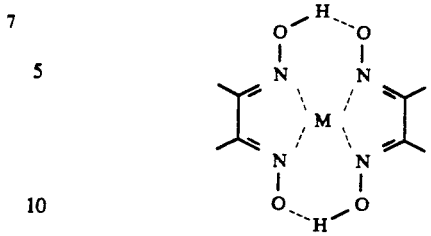

14

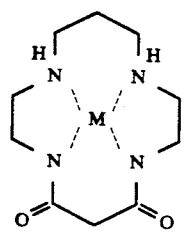

8

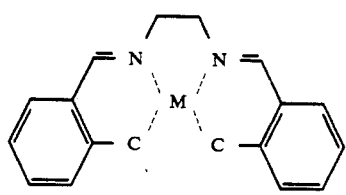

9

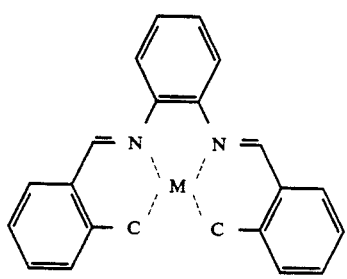

10

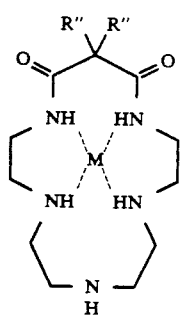

11

R″ = fluorine, alkyl or aryl

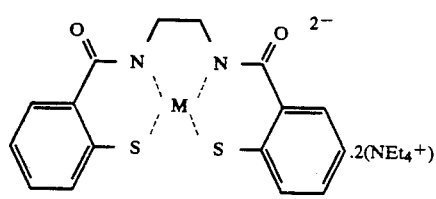

13

21. A kit for a nucleic acid assay for locating guanine groups in nucleic acids having labelled 5′-ends, said nucleic acids comprising nucleotides, oligonucleotides, polynucleotides, RNA and single-stranded DNA and double-stranded DNA containing non-base paired guanine groups, said kit comprising;

(a) a metal complex comprising structures I, II or III:

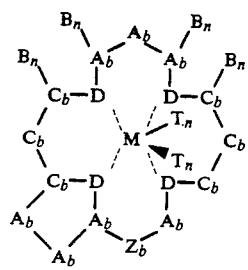

I

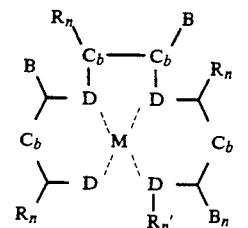

II

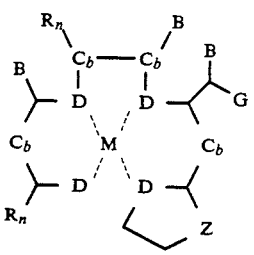

III wherein:
A independently represents carbon or oxygen;
B independently represents doubly bonded oxygen;
C represents carbon;
D independently represents nitrogen, oxygen or sulfur;
M represents a metal ion;
T represents an anion which can be replaced by water in solution;
Z independently represents carbon or nitrogen;
b=0-5;
n=0-1;
R independently represents $(CH_2)_3NH_2$, $(CH_2)_4NH_2$,

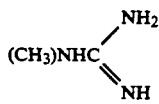

or hydrogen; except that all R radicals in one structure do not represent hydrogen and all n values in $R_n$ in one structure do not equal zero;

R' represent hydrogen, alkyl, aryl or a polypeptide chain;

G represents OH, OR, a simple amide or a DNA delivery agent; wherein all atoms contain sufficient bonds to adjacent atoms, to hydrogen substitutes of claim 1 or to hydrogen to result in a stable structure;

(b) an oxidant selected from the group consisting of peracid, hypochlorite, $O_2$, peroxide in combination with ascorbate and $O_2$ in combination with ascorbate; and (c) a base selected from the group consisting of piperidine, N-butylamine and sodium hydroxide, whereby the presence of labelled 5'-ends can be detected, and the detection and electrophoretic migration of labelled ends correlates with the location of guanine groups.

22. The kit of claim 21 wherein the metal is selected from the group consisting of $Ni^{2+}$, $Co^{2+}$, $Cu^{2+}$, $Rh^{2+}$, $Pd^{2+}$, $Ir^{2+}$, $Pt^{2+}$, $Cr^{2+}$, $Mn^{2+}$, $Fe^{2+}$, $Ru^{2+}$ and $Os^{2+}$.

23. The kit of claim 21 wherein the metal is selected from the group consisting of $Ni^{2+}$, $Co^{2+}$ and $Pd^{2+}$.

24. The kit of claim 21 wherein the structure of the metal complex includes a delivery agent selected from the group consisting of intercalators, groove-binding agents, oligonucleotides, protein fragments, and polyamines.

25. The kit of claim 24 wherein the intercalator is selected from the group consisting of ethidium, methidium, acridine, proflavin and phenanthroline.

26. The kit of claim 24 wherein the groove-binding agent is distamycin or netropsin.

27. The kit of claim 24 wherein the oligonucleotide has a nucleotide sequence which enables it to form a double or triple helical area with the target nucleotide.

28. The kit of claim 24 wherein the protein fragment is derived from Hin recombinase or another DNA-binding protein.

29. The kit of claim 24 wherein the polyamine is spermine or spermidine.

30. The kit of claim 21 wherein the peracid is selected from the group consisting of potassium peroxymonosulfate, magnesium monoperoxyphthalate, peroxide and alkylhydroperoxide.

31. The kit of claim 21 wherein the 5'-ends are labelled with $^{32}P$.

* * * * *

UNITED STATES PATENT AND TRADEMARK OFFICE
CERTIFICATE OF CORRECTION

PATENT NO. : 5,272,056
DATED : December 21, 1993
INVENTOR(S) : Burrows et al.

Page 1 of 6

It is certified that error appears in the above-identified patent and that said Letters Patent is hereby corrected as shown below:

|  | READS | SHOULD READ |
|---|---|---|
| Column 3, Structure I, |  |  |
| Column 4, structure 1, | 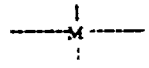 | 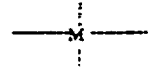 |
| Column 5, structure 5, | 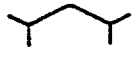 |  |
| Column 5, structure 9, |  |  |
| Column 6, structure 10, | 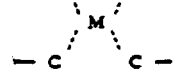 | 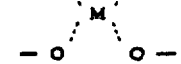 |
| Column 14, Line 32, | $NiL_1^{2-}+$ | $NiL_1^{2+}$ |

UNITED STATES PATENT AND TRADEMARK OFFICE
CERTIFICATE OF CORRECTION

PATENT NO. : 5,272,056
DATED : December 21, 1993
INVENTOR(S) : Burrows et al.

It is certified that error appears in the above-identified patent and that said Letters Patent is hereby corrected as shown below:

| | READS | SHOULD READ |
|---|---|---|
| Column 15, Complex 2, | (solid bond Ni structure) | (dashed bond Ni structure) |
| Column 15, Complex 3, | (solid bond Cu structure) | (dashed bond Cu structure) |
| Column 15, Complex 4, | (solid bond Ni structure) | (dashed bond Ni structure) |
| Column 15, Complex 5, | (solid bond Cu structure) | (dashed bond Cu structure) |
| Column 16, Complex 9, | (structure without arcs) | (structure with arcs) |

UNITED STATES PATENT AND TRADEMARK OFFICE
CERTIFICATE OF CORRECTION

PATENT NO. : 5,272,056
DATED : December 21, 1993
INVENTOR(S) : Burrows et al.

It is certified that error appears in the above-identified patent and that said Letters Patent is hereby corrected as shown below:

Column 17, Line 19, reads "led to significant amounts (lanes 4 and 5)." should read --led to significant amounts of DNA modification as judged by piperidine treatment (lanes 4 and 5).--;

Column 17, Line 26, reads "NiL$_{5+}$", should read --NiL$_5^+$--;

|  | READS | SHOULD READ |
|---|---|---|
| Column 19, Claim 1, Structure I, |  |  |
| Column 20, Claim 2, Structure 1, | 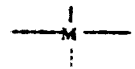 | 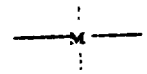 |
| Column 20, Claim 2, Structure 5, | 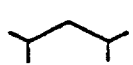 |  |

UNITED STATES PATENT AND TRADEMARK OFFICE
CERTIFICATE OF CORRECTION

PATENT NO. : 5,272,056
DATED : December 21, 1993
INVENTOR(S) : Burrows et al.

It is certified that error appears in the above-identified patent and that said Letters Patent is hereby corrected as shown below:

Column 21,

Claim 2, Structure 9,

Column 21,

Claim 2, Structure 10, 

Column 23,

Claim 19, Structure 1, 

Column 23,

Claim 20, Structure 1, 

UNITED STATES PATENT AND TRADEMARK OFFICE
CERTIFICATE OF CORRECTION

PATENT NO. : 5,272,056

DATED : December 21, 1993

INVENTOR(S) : Burrows et al.

It is certified that error appears in the above-identified patent and that said Letters Patent is hereby corrected as shown below:

|  | READS | SHOULD READ |
|---|---|---|
| Column 24, Claim 20, Structure 5, | 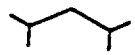 |  |
| Column 25, Claim 20, Structure 9, |  | 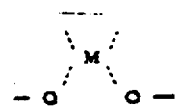 |
| Column 25, Claim 20, Structure 10, | 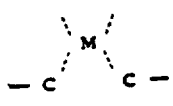 | 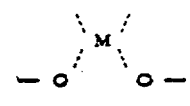 |
| Column 26, Claim 21, Structure I, |  |  |

UNITED STATES PATENT AND TRADEMARK OFFICE
CERTIFICATE OF CORRECTION

PATENT NO. : 5,272,056
DATED : December 21, 1993
INVENTOR(S) : Burrows et al.

It is certified that error appears in the above-indentified patent and that said Letters Patent is hereby corrected as shown below:

Column 28,

Claim 22, Line 2, reads "$Ni^{2+}Co^{2+}$" should read --$Ni^{2+}$, $Co^{2+}$--;

Signed and Sealed this

Twentieth Day of December, 1994

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,272,056

DATED : December 21, 1993

INVENTOR(S) : Burrows et al.

It is certified that error appears in the above-identified patent and that said Letters Patent is hereby corrected as shown below:

Page 1 of 2

|  | READS | SHOULD READ |
|---|---|---|
| Column 5, structure 6, | 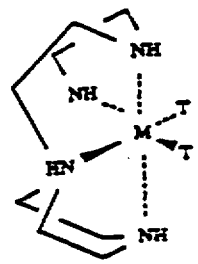 | 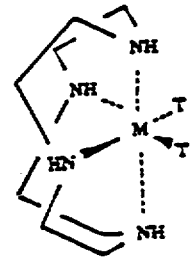 |
| Column 16, Complex 10, | 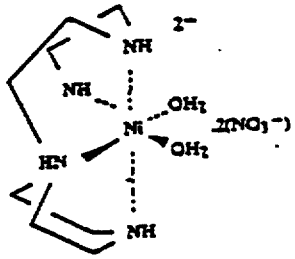 | 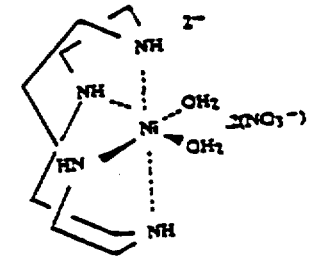 |
| Column 21:<br><br>Claim 2, Structure 6, | 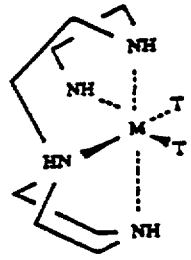 | 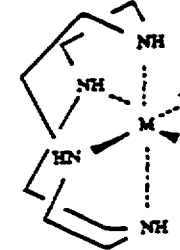 |

UNITED STATES PATENT AND TRADEMARK OFFICE
CERTIFICATE OF CORRECTION

PATENT NO. : 5,272,056
DATED : December 21, 1993
INVENTOR(S) : Cynthia J. Burrows, et al.

It is certified that error appears in the above-indentified patent and that said Letters Patent is hereby corrected as shown below:

Column 24:

Claim 20, Structure 6, 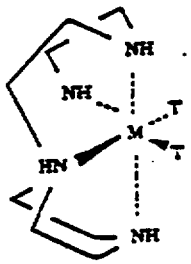 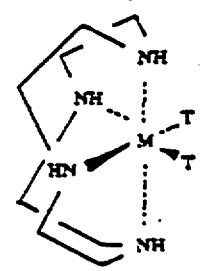

Signed and Sealed this

Twenty-eight Day of March, 1995

Attest:

BRUCE LEHMAN

Attesting Officer     Commissioner of Patents and Trademarks